United States Patent [19]

Wallace

[11] Patent Number: 5,210,783
[45] Date of Patent: May 11, 1993

[54] PENETRAMETER AND METHOD OF USE

[75] Inventor: Harry L. Wallace, Kennesaw, Ga.

[73] Assignee: Lockheed Corporation, Calabasas, Calif.

[21] Appl. No.: 892,880

[22] Filed: Jun. 3, 1992

[51] Int. Cl.⁵ ............................................. G01D 18/00
[52] U.S. Cl. ..................................... 378/207; 378/162
[58] Field of Search ................................ 378/207, 162

[56] References Cited

U.S. PATENT DOCUMENTS 5,095,499 3/1992 Wentz ................................ 378/207

Primary Examiner—Craig E. Church
Attorney, Agent, or Firm—Eric R. Katz

[57] ABSTRACT

A penetrameter is provided for use in evaluating the resolution of an x-ray inspection system as well a method for calibrating the resolution of the x-ray inspection system. The penetrameter comprises a radiolucent substrate, and at least one filament at the radiolucent substrate, the at least one filament being broken by a gap having a predetermined size. The method of determining the resolution of an x-ray inspection system comprises steps of: generating a radiographic image of the penetrameter, determining if the broken filament is visible, and if the broken filament is visible, determining if the gap is visible.

12 Claims, 4 Drawing Sheets

PENETRAMETER AND METHOD OF USE

BACKGROUND OF THE INVENTION

1. Field of the Invention

The present invention relates to a penetrameter for use in the x-ray analysis of a broad range of different materials as well as to a method for calibrating the resolution of an x-ray inspection system used to conduct non-destructive evaluation of such materials.

2. Background Discussion

Radiographic and radioscopic data acquisition systems, are useful tools in the non-destructive evaluation (NDE) of both metallic and non-metallic materials using x-ray analysis. Flaws detectable using x-ray analysis include, but are not limited to, corrosion, material density anomalies, useful in revealing subtle low-density inclusions and voids in advanced composite material parts, and fiber discontinuity in composite materials.

FIG. 1 illustrates the basic principles of operation of a radiographic data acquisition system, generally indicated at 11, which typically employs an x-ray source 13 to provide a beam of x-rays 15 that impacts an object or part 17 to be analyzed. A detector 19, in the form of a photographic plate, is positioned to receive the x-rays that pass through and are scattered by the part 17. After exposure of the photographic plate to the x-rays, the plate is developed to form a shadow image or radiograph of the part 17. The radiograph is then use to conduct an analysis of the material structure of the part 17.

Referring to FIG. 2, one illustration of a radioscopic data acquisition system 21 is provided wherein the x-ray source 23 of the system 21 sends out a beam of x-rays 25 that passes through a specimen or part 27. The beam of x-rays 25 is then detected by an intensifier 29, connected to a CCD camera 31 which, in this case, is connected at its output to a image processor 33 that makes available an image which is displayed on a video monitor 35.

Thus, a radioscopic system is a non-film x-ray imaging system whereas the radiographic system is a film x-ray imaging system. The primary advantages of radioscopy over radiography is speed of operation and the ability to examine outsized, multi-configured structures.

A standard test piece is usually included in radiography and radioscopy systems as a check on the adequacy of the associated technique. The test piece is commonly referred to as a penetrameter in North America and an Image Quality Indicator (IQI) in Europe. Although applicable to both radioscopic and radiographic analysis, for the sake of simplicity, the following discussion will be limited to radiographic applications.

The penetrameter is typically a simple geometric form made of the same material as, or a material similar to, the specimen being radiographed. It includes some small structures (holes, wires, etc.) and is provided with a given thickness, the dimensions of both of which can bear some numerical relation to the thickness of the part being tested. This relationship is typically denoted in terms of some percentage value, i.e., the thickness of the penetrameter or diameter of the holes being a percentage of the thickness of the part being imaged.

In use the penetrameter is placed at the part and imaged therewith. Then, the smallest feature of the penetrameter visible on the resulting radiograph is determined, the quality level of the radiograph being determined thereby. For example, if the penetrameter has a thickness that is 2% of the thickness of the part and a hole therein has a diameter that is 1% of the thickness of the part and only the outline of the penetrameter is visible in the radiograph and not the hole, then the quality level is typically designed as being 2%.

The image of the penetrameter on the radiograph is permanent evidence that the radiographic examination was conducted under proper conditions. The use of penetrameters is advisable because they provide an effective check on the overall quality of the radiographic inspection.

Common penetrameters consist of a small rectangular piece of metal 39, as seen in FIG. 3A, or a circular piece of metal 41, as seen in FIG. 3B, containing several (usually three) holes 43, the diameters of which are related to the thickness of the penetrameter. Another penetrameter design also used, as best seen in FIG. 3C, is the German DIN (Deutsche Industrie-Norm) penetrameter which consists of a number of parallel metal wires 47 of various diameters sealed in a plastic envelope 45. The image quality is indicated by the thinnest wire visible on the radiograph. The DIN penetrameter system is such that only three penetrameters, each containing seven wires, can cover a wide variety of specimen thickness.

The hole type penetrameter, as seen in FIGS. 3A and 3B, is essentially a go, no-go gauge which indicates whether a specified quality level or resolution level has been attained, but in most cases does not indicate whether the requirements have been exceeded, or by how much. The DIN penetrameter, as seen in FIG. 3C, on the other hand is a series of seven penetrameters in a single unit. As such, the DIN penetrameter has the advantage that the radiographic quality level achieved can often be read directly from the process radiograph.

However, the DIN penetrameter is typically used in connection which metal parts which do not include fibers as are commonly included in composite parts. As a result of the parallel configuration of the metal wires of the DIN penetrameter, these metal wires are often difficult to distinguish from the fibers of the composite material which are also typically oriented in a parallel configuration.

As described above, in use, the penetrameter is placed with the specimen and a radiograph of the specimen and penetrameter is made. By examining the radiograph of the penetrameter to determine the smallest sized structure visible, it is possible to determine and evaluate the resolution level of the radiograph.

A recent development in the field of NDE using x-ray analysis is the use of low kilovoltage radiography and radioscopy which is a specific x-ray technology employing very low X-radiation (generally between about 7 and 30 kilovolts) while increasing the x-ray tube filament milliamperage. Due to the increased x-ray tube electron flux, the effective focal spot must have a greater surface dimension than used with standard x-ray techniques. Most carbon based composite materials have a reduced level of absorption to x-ray energies and therefore, the lower KV ranges provide higher radiographic contrast for such evaluations.

The design and make up of the above-noted, known penetrameters, however, are not compatible with the improvements in low kilovolt radiography system resolution because these known penetrameters essentially function as go, no-go gages. With the increased radiographic contrast and sensitivity that very low kilovoltage radiography offers, a more representative penetrameter is needed to judge the adequacy of the imaging technique as well as to serve as an anomaly analysis aid, particularly when conducting a NDE of a composite part having fibers.

SUMMARY OF THE INVENTION

Accordingly, it is an object of the present invention to provide a penetrameter and method for x-ray system resolution evaluation specifically adapted for use with low kilovoltage radiography and radioscopy techniques.

It is a further object of the present invention to provide a penetrameter and method of use which reliably and accurately calibrate, for standardization, the resolution of an x-ray inspection system.

It is a yet another object of the present invention to provide a penetrameter and method of use which is particularly adapted for utilization in the NDE x-ray analysis of composite materials including fibers as well as a scrim cloth component.

One particularly advantageous feature of the present invention is that the penetrameter is capable of use for multiple part thicknesses. The design features of the penetrameter of the present invention incorporate several different diameters (thicknesses) of nylon filaments that equate to percent thickness representations similar to that found in DIN penetrameters. The range of filament thicknesses and their clocked arrangement make the penetrameter of the present invention effective due to the matching of normal industry part available thicknesses and ply lay-up orientations most frequently employed. As a result of the clocked arrangement of the filaments of the penetrameter of the present invention, the filaments are more easily distinguished from the fiber of the composite material due to the angular offset therebetween.

Yet another advantageous feature of the present invention is that the penetrameter is provided with an arrangement which permits evaluation of the resolution of the x-ray inspection system for use in connection with determining the presence of broken fibers in composite parts, as well as the unintentional inclusion of a scrim cloth component which is typically characterized as an desirable porosity.

Still another advantageous feature of the present invention is that the penetrameter provides a diagnostic indicator for evaluating minimal flaw size detectability provided by a given x-ray inspection system.

A further advantageous feature of the present invention is that the penetrameter functions as an anomaly analysis aid by providing the provision of broken filament and a scrim cloth. Therefore, a image of what a broken fiber or the inclusion of an unwanted scrim cloth component is provided by the penetrameter of the present invention which permits the technician to compare a standard image of an anomaly with those included in the part.

These and other objects, advantages and features of the present invention are achieved, according to one embodiment thereof, by a penetrameter comprising a radiolucent substrate and at least one filament at the radiolucent substrate, the at least one filament being broken by a gap of a predetermined size.

According to a further embodiment of the present invention, the penetrameter comprises a radiolucent disc having a plurality of radially extending filaments arranged in a clocked order configuration wherein each of the filaments has a different filament diameter. Respective filament diameters of the plurality of filaments preferably are 0.025 inch, 0.013 inch, 0.010 inch, 0.008 inch, 0.005 inch, 0.003 inch, and 0.0025 inch. A 5 mil thick square of nylon scrim cloth, for example, is also provided at a center of the disc and the 0.005 inch diameter filament is separated by, for example, a 0.120 break, the 0.005 inch diameter filament being preferably made of carbon, for example, graphite, other of the filaments being made of, for example, nylon.

The broken 0.005 inch diameter filament is used for 1% quality level or resolution level for specific and generic composite materials and for defect characterizations. The degree of separation provided by the broken filament, when clearly visualized on a radiograph, depicts an anomalous condition that has been extremely difficult to image in standard composites radiography. The 1% quality level is designated as the best achievable condition due to this fact. The provision of a broken filament is preferred when defect recognition and optimum radiographic sensitivity are indicated and is applicable in the evaluation of both thermoplastic and thermosetting materials.

DETAILED DESCRIPTION OF THE PREFERRED EMBODIMENT(S)

Because the specific nature of certain composite materials is their low radiation absorption qualities, the materials which comprises the penetrameter of the present invention are selected to be a match or a near match to the low radiation absorption qualities of the composite materials to be imaged. This is important in establishing a more realistic assessment of actual part density variations verses the assessment of representative density changes found in the penetrameter.

Figure 1:
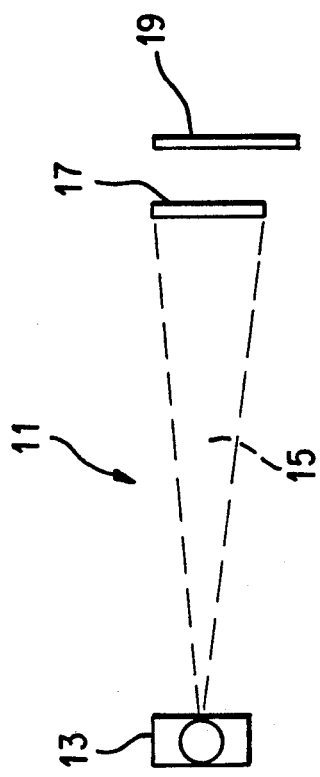
FIG. 1 schematically illustrates the operation of a radioscopic data acquisition system.
Figure 2:
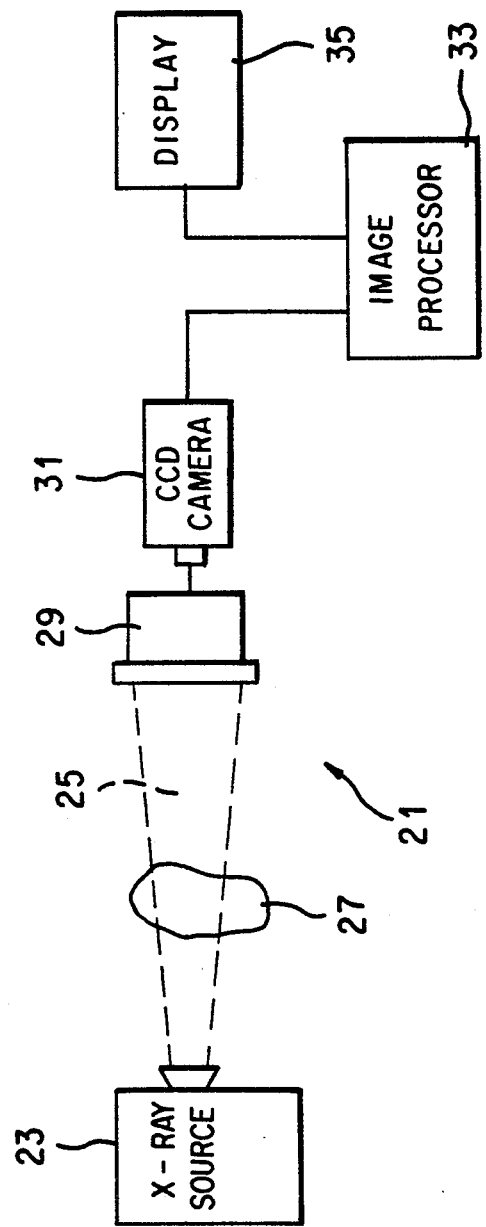
FIG. 2 illustrates a known radioscopic data acquisition system for the non-destructive evaluation (NDE) of materials using x-ray analysis.
Figure 3A:
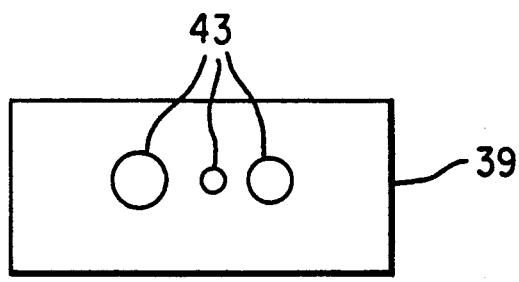
FIGS. 3A-3C are front, planar views of known penetrameters used to evaluate the resolution of an x-ray inspection system.
Figure 3B:
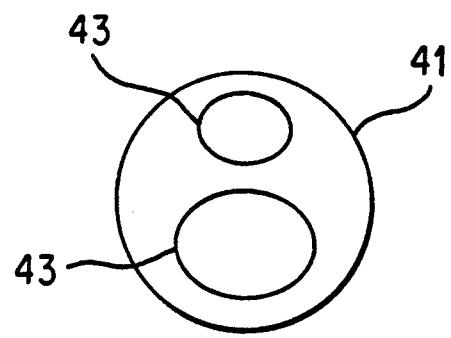
Figure 3C:
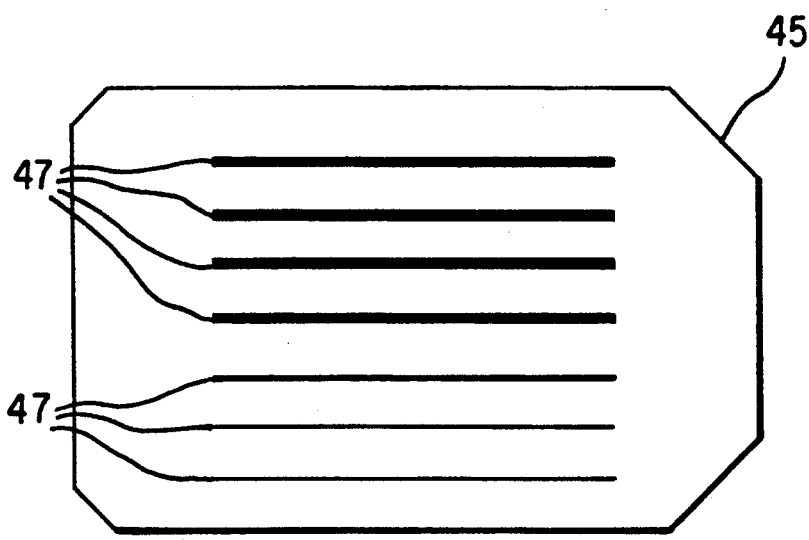
Figure 4:
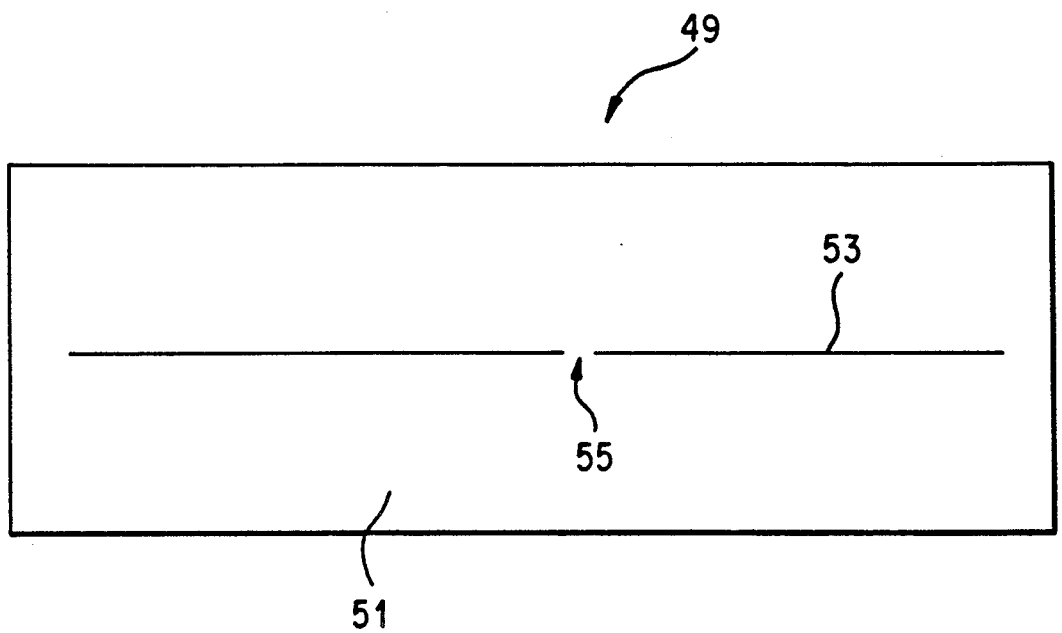
FIG. 4 is a front, planar view illustrating one embodiment of the penetrameter according to the present invention.

Referring to FIG. 4, one embodiment of the penetrameter of the present invention is illustrated generally at 49 which comprises a substrate 51 including a broken filament 53 which is broken by a gap, generally indicated at 55, having a predetermined size. The substrate 51 preferably comprises a radiolucent material, for example, a celluloid material such as polyester and the broken filament 53 is preferably made of carbon, for example, graphite.

A filament diameter of the broken filament 53 is preferably on the order of about 0.005 inch and the predetermined size of the gap 55 is preferably on the order of about 0.120 inch when the penetrameter is to be used to evaluate composite materials. However, as is understood by the skilled artisan, the present invention is not limited to the above recited dimensions and materials, which can be altered in accordance with the type of material being evaluated and the degree of resolution required.

Figure 5A:
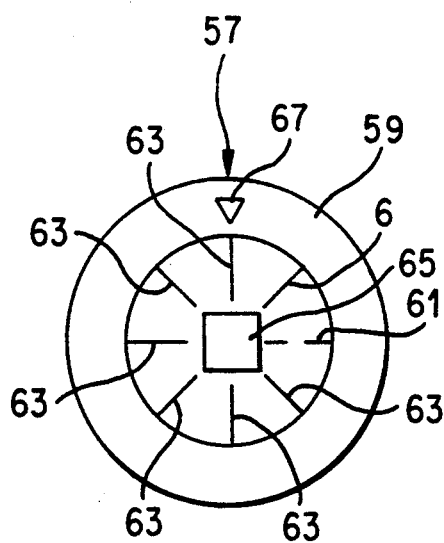
FIGS. 5A-5B are front and side views respectively of a further embodiment of the present invention.
Figure 5B:
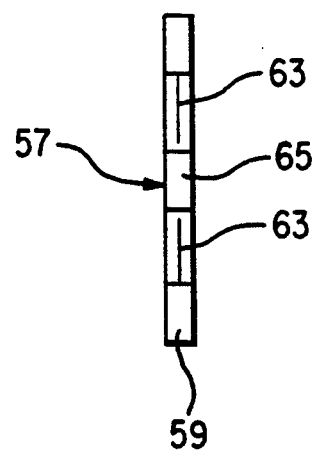

Referring to FIGS. 5A-5B, a further embodiment of the penetrameter of the present invention is generally illustrated at 57. The penetrameter 57 comprises a radiolucent disc 59 made of, for example, celluloid, such as polyester, the disc 59 having a broken filament 61 made of, for example, carbon such as graphite, and a plurality of unbroken filaments 63, made of, for example, nylon. At the center of the disc 59 is provided a scrim cloth 61 made of, for example, nylon.

The broken filament 61, plurality of unbroken filaments 63 and the scrim cloth 65 are attached to a surface of the disc 59 by an adhesive tape or the like, made of, for example, cellophane or plastic. An indicator 67, made of a material which is at least opaque to x-rays, is provided as a reference point to indicate the position of the various filaments of the penetrameter 57 as will be more fully described hereinafter.

The plurality of filaments 61, 63 are preferable radially extending and arranged in a predetermined clocked order relative to the indicator 67. Because the unbroken filaments 63 have decreasing diameters, the indicator 67 provides a reference point to permit a user to determine the diameter of each of the filaments 63 by determining the filament's position relative to the indicator 67.

Respective filament diameters of the plurality of filaments 61, 63 preferably are 0.025 inch, 0.013 inch, 0.010 inch, 0.008 inch, 0.005 inch, 0.003 inch, and 0.0025 inch. In the present embodiment, a 5 mil thick square of nylon scrim cloth 65, for example, is also provided at the center of the disc 59 and the 0.005 inch diameter filament is the broken filament 61 which is broken by, for example, a gap of about 0.120 inch.

Figure 6:
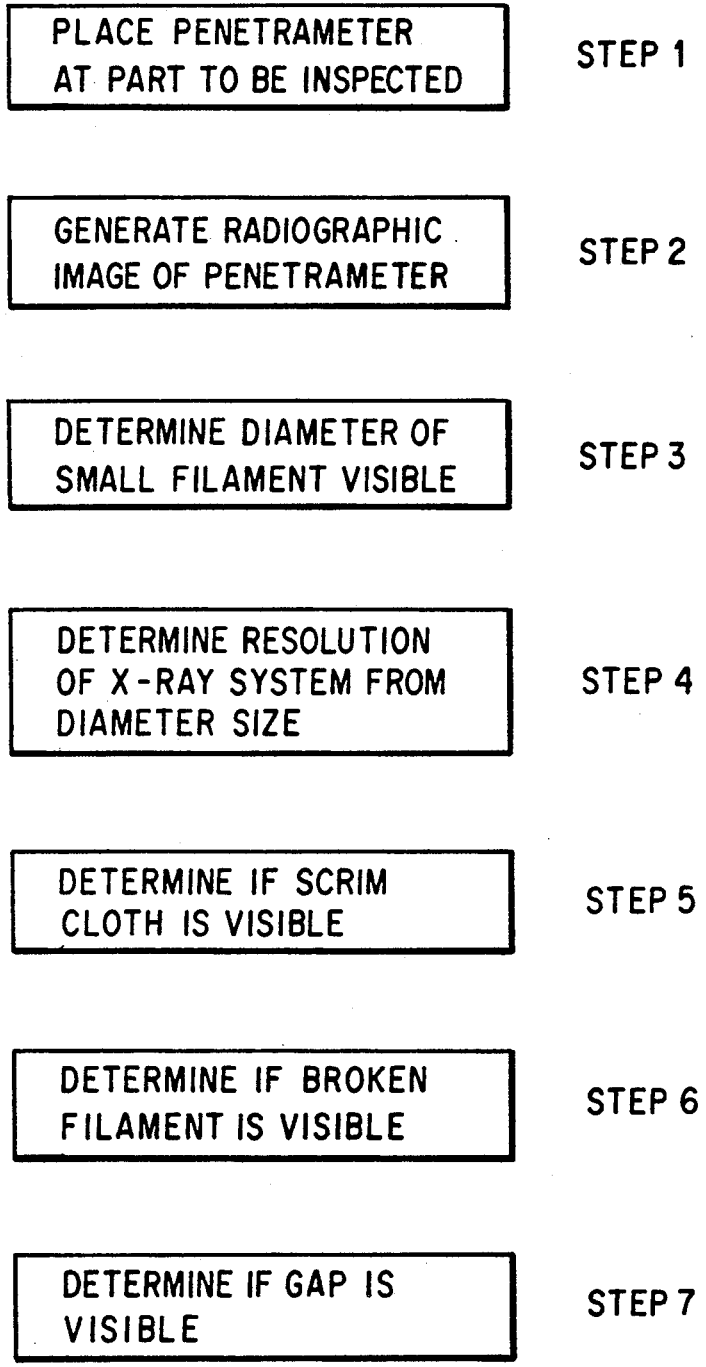
FIG. 6 is a block diagram illustration one embodiment of a method of using the penetrameter of the present invention.

Referring to FIG. 6, one embodiment of the method of the present invention is illustrated by a block diagram. In use, the penetrameter is placed, in step 1, at the part to be evaluated, for example on the source side of the part. In step 2, a radiograph or radioscopic image of the part with the penetrameter is made.

The plurality of filaments 63, which are provided with decreasing diameters, allude to the sensitivity range or resolution of the x-ray inspection system. Therefore, in step 3, by viewing the radiograph of the penetrameter, the diameter of the thinnest filament visible is determined. In step 4, the resolution of the x-ray system is determined by referring to a look-up table, prepared by empirical data, which ties the diameter of each of the filaments to a given level of resolution of the x-ray inspection system.

In step 5, a determination is made as to whether or not the scrim cloth is visible. Then, in step 6, a further determination is made as to whether or not the broken filament is visible and, in step 7, if it is visible, a determination is made as to whether or not the gap can be seen on the radiograph. The visualization of the scrim cloth and the gap represent the maximum sensitivity capabilities of the radiographic technique.

Although the present invention has been described with particular reference to its preferred embodiments, it should be understood that many variations and modifications will now be obvious to those skilled in that art, and it is preferred, therefore, that the scope of the invention be limited, not by the specific disclosure herein, but only by the appended claims.

What is claimed is:

1. A penetrameter comprising:
    a radiolucent substrate; and
    at least one filament at the radiolucent substrate;
    wherein the at least one filament is broken by a gap having a predetermined size.

2. A penetrameter according to claim 1, wherein the predetermined sized of the gap is approximately a 0.120 inch break in the at least one filament.

3. A penetrameter according to claim 1, wherein the at least one filament is carbon.

4. A penetrameter according to claim 1, wherein the at least one filament further comprises a plurality of filaments arranged is a clocked configuration and wherein each of the plurality of filaments has a different filament diameter.

5. A penetrameter according to claim 1, further comprising a scrim cloth at the radiolucent substrate.

6. A penetrameter according to claim 1, wherein the substrate is a disc.

7. A penetrameter according to claim 6, wherein the at least one filament further comprises a plurality of filaments arranged in a clock configuration and wherein the plurality of filaments have different filament diameters which are each related to the clocked position of a given filament.

8. A penetrameter according to claim 7, wherein the scrim cloth is at a center of the radiolucent substrate.

9. A penetrameter according to claim 8, wherein filament diameters of the plurality of filaments include filament diameters which are approximately 0.025 inch, 0.013 inch, 0.010 inch, 0.008 inch, 0.005 inch, 0.003 inch, and 0.0025 inch, respectively.

10. A penetrameter according to claim 8, wherein the predetermined size of the gap is a 0.120 inch break; wherein the filament having a 0.005 inch diameter is provided with the gap; wherein filament having the 0.005 inch diameter is made of graphite and wherein all other filaments are made of nylon.

11. A penetrameter according to claim 1, wherein the substrate is made of celluloid.

12. A method of determining the resolution of an x-ray inspection system comprising the steps of:
    generating a radiographic image of a penetrameter including a plurality of filaments having different diameters, at least one of the filaments being a broken filament broken by a gap of predetermined size;
    determining if the broken filament is visible; and
    if the broken filament is visible, determining if the gap is visible.

* * * * *